(12) United States Patent
Sutarlie et al.

(10) Patent No.: US 11,371,938 B2
(45) Date of Patent: Jun. 28, 2022

(54) NANOMATERIAL-BASED BACTERIAL SENSORS

(71) Applicant: AGENCY FOR SCIENCE, TECHNOLOGY AND RESEARCH, Singapore (SG)

(72) Inventors: Laura Sutarlie, Singapore (SG); Sian Yang Ow, Singapore (SG); Shilin Chen, Singapore (SG); Xiaodi Su, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 390 days.

(21) Appl. No.: 16/491,960

(22) PCT Filed: Mar. 27, 2018

(86) PCT No.: PCT/SG2018/050137
§ 371 (c)(1),
(2) Date: Sep. 6, 2019

(87) PCT Pub. No.: WO2018/182510
PCT Pub. Date: Oct. 4, 2018

(65) Prior Publication Data
US 2020/0158642 A1    May 21, 2020

(30) Foreign Application Priority Data

Mar. 28, 2017 (SG) .......................... 10201702528R

(51) Int. Cl.
| | | |
|---|---|---|
| *G01N 21/64* | (2006.01) | |
| *G01N 15/06* | (2006.01) | |
| *G01N 21/359* | (2014.01) | |
| *G01N 33/542* | (2006.01) | |

(Continued)

(52) U.S. Cl.
CPC ......... *G01N 21/6428* (2013.01); *G01N 15/06* (2013.01); *G01N 21/359* (2013.01);

(Continued)

(58) Field of Classification Search
CPC .. G01N 21/6428; G01N 15/06; G01N 21/359; G01N 33/542; G01N 33/56916;

(Continued)

(56) References Cited

U.S. PATENT DOCUMENTS

2002/0051985 A1* 5/2002 Whitten ............. G01N 21/6428
435/6.19
2003/0044805 A1* 3/2003 Mirkin ................... B82Y 30/00
435/6.12

(Continued)

FOREIGN PATENT DOCUMENTS

| CN | 105424927 A | 3/2016 | |
|---|---|---|---|
| CN | 106086173 A | 11/2016 | |
| WO | WO-2016208466 A1 * | 12/2016 | ........... G01N 33/542 |

OTHER PUBLICATIONS

Lim et al., "Peptide-Assembled Graphene Oxide as a Fluorescent Turn-On Sensor for Lipopolysaccharide (Endotoxin) Detection", 2015, Anal. Chem., 87, 9408-9412 (Year: 2015).*

(Continued)

*Primary Examiner* — Samuel P Siefke
*Assistant Examiner* — Henry H Nguyen
(74) *Attorney, Agent, or Firm* — Marshall, Gerstein & Borun LLP

(57) ABSTRACT

This disclosure relates to a sensor that detects bacteria cells comprising (a) a primary negatively charged, nanoparticulate sensing material; (b) a secondary positively charged, fluorescent sensing material; (c) a housing; and (d) at least one illuminator. This disclosure further relates to a method for detecting bacteria cells.

18 Claims, 12 Drawing Sheets

Specification includes a Sequence Listing.

(51) Int. Cl.
    *G01N 33/569* (2006.01)
    *B82Y 15/00* (2011.01)
    *G01N 15/00* (2006.01)

(52) U.S. Cl.
    CPC ..... *G01N 33/542* (2013.01); *G01N 33/56916* (2013.01); *G01N 33/56938* (2013.01); *B82Y 15/00* (2013.01); *G01N 2015/0065* (2013.01); *G01N 2015/0681* (2013.01); *G01N 2015/0687* (2013.01); *G01N 2015/0693* (2013.01); *G01N 2021/6432* (2013.01)

(58) Field of Classification Search
    CPC ..... G01N 33/56938; G01N 2015/0065; G01N 2015/0681; G01N 2015/0687; G01N 2015/0693; G01N 2021/6432; G01N 21/6452; B82Y 15/00
    See application file for complete search history.

(56) References Cited

U.S. PATENT DOCUMENTS

2006/0127929 A1* 6/2006 Swager ................ G01N 33/542
    435/6.12
2009/0270269 A1* 10/2009 Kumar ................ G01N 33/542
    506/9
2010/0021960 A1 1/2010 Rotello et al.
2016/0340717 A1* 11/2016 McNamara ........ G01N 21/6428

OTHER PUBLICATIONS

Translation of WO2016208466A1, Abe, Ryoji, Dec. 29, 2016 (Year: 2016).*

Search Report and Written Opinion in International Application No. PCT/SG2018/050137 dated Jun. 12, 2018, 9 pages.

Yu et al., "Dual-Recognition Förster Resonance Energy Transfer Based Platform for One-Step Sensitive Detection of Pathogenic Bacteria Using Fluorescent Vancomycin-Gold Nanoclusters and Aptamer-Gold Nanoparticles", Analytical Chemistry, vol. 89, Mar. 13, 2017, pp. 4085-4090.

Ramos et al., "Composites of Bromobenzenethiol Functionalized Gold Nanoparticles and the Fluorescent Poly(Phenylene Ethynylene) pPET30C12-sqS for Optical Biosensors", Journal of Nano Research, vol. 5, Feb. 6, 2009, pp. 37-46.

* cited by examiner

NANOMATERIAL-BASED BACTERIAL SENSORS

This application contains, as a separate part of disclosure, a sequence listing in computer-readable form (filename: 54692_SeqListing.txt; 529 bytes; created: Dec. 31, 2019) which is incorporated by reference in its entirety.

TECHNICAL FIELD

The present invention generally relates to a sensor to rapidly detect bacteria in an aqueous medium. The sensor may be used in a fluorometric assay based on the fluorescence resonance energy transfer (FRET) phenomenon of the sensing materials. The sensing materials are positively charged luminescent materials and negatively charged nanomaterials. The sensor and the related method allow the determination of a total bacteria count.

BACKGROUND ART

Bacteria detection and quantification are important for health and safety. Many of the current standards methods for bacteria detection rely on laboratory-based bacteria plate counting or PCR, which are time consuming (in hours or days). There is a need for rapid bacteria detection, which can be portable and suitable for on-site applications. There are numerous potential applications for a total bacteria count sensor. For instance this can be used as an indicator to the possible presence of pathogenic bacteria.

Rapid detection methods for total bacteria have been developed, such as the Bactiquant® system by mycometer. The Bactiquant system targets the hydrolase enzymes of bacteria. The reaction of these bacteria enzymes with a substrate creates a luminescence signal. Another method relies on the detection of ATP (adenosine triphosphate). ATP is a molecule found in and around living cells, such as bacteria, and as such it allows a direct measure of biological bacteria concentration. ATP is quantified by measuring the light produced through its reaction with the naturally occurring firefly enzyme luciferase, using a luminometer. Both methods can be used in portable devices and allow rapid determination of the total bacteria count. They can also distinguish living and dead bacteria. However, due to the use of enzymes which are sensitive to pH and temperature change, they cannot be used in an environment with wide pH and temperature ranges. Furthermore their detection limits are not always satisfactory under various application conditions.

There is therefore a need for another method or sensor system for rapid bacteria detection, which can be portable and suitable for on-site applications. There is specifically a need for a sensor that can easily and rapidly measure the total bacteria count without being specific to a certain bacteria type. For a broad range of applications there is also the need for a detection method that is not sensitive to coloration and other impurities in aqueous bacteria-containing samples which interfere with the detection results. The sensor shall further be mostly sensitive to harmful living bacteria and not to dead bacteria.

SUMMARY OF INVENTION

The first aspect of the invention is a sensor that detects bacteria cells comprising (a) a primary negatively charged, nanoparticulate sensing material; (b) a secondary positively charged, fluorescent sensing material; (c) a housing; and (d) at least one illuminator; wherein said housing contains said primary negatively charged, nanoparticulate sensing material, said secondary positively charged, fluorescent sensing material, and a sample potentially comprising bacteria in aqueous medium, wherein said illuminator provides light of at least one pre-specified wavelength $\lambda_i$ to excite at least said secondary positively charged, fluorescent material, wherein said secondary positively charged, fluorescent material electrostatically attached to bacteria cells provides at least one fluorescent response at a second different wavelength $\lambda_n$, wherein both i and n are integers, wherein said negatively charged, nanoparticulate sensing material electrostatically attached to said fluorescent material suppresses fluorescing of said fluorescent material at said second wavelength $\lambda_n$; and wherein said housing permits illumination of the contents of said housing by said illuminator and wherein said housing further permits the detection of a fluorescent response at a second wavelength $\lambda_n$.

Advantageously, the sensor can be used to measure the total bacteria count by detecting the fluorescence intensity in the presence of the bacteria of the sample. It avoids the use of enzymes because the sensing principle is based on a competitive FRET phenomenon and on electrostatic interaction. Most bacteria have a negatively charged surface due to lipopolysaccharides or teichoic acids on the cell wall. The sensor is designed to target to this common property of bacteria cells, according to the secondary sensing material. The primary negatively charged sensing material as a fluorescence quencher competes with bacteria cells for attaching to the secondary positively charged fluorescent materials which defines the sensing principle. Advantageously, such sensor is stable over a wider range of pH and temperature. The presence of bacteria and the total amount of the bacteria are detected and determined by their influence on the FRET phenomenon between the primary and secondary sensing materials. No interaction with an enzyme is needed. The bacteria cells interfere with the FRET phenomenon and are therefore detectable.

Advantageously, the sensor according to the invention can deliver a result in 15 min, with minimal hands-on steps. The 15 min detection time is a significant advantage over the standard bacteria culture method (1 to 3 days). Furthermore the sensors can provide quantitative measurement in a large dynamic range of 1 to $10^8$ cfu/ml and differentiate live and dead bacteria. The tuneable limit of detection (LOD) and the sensor's large dynamic range are particularly practical for bacterial detection in different field samples. The raw material used for the sensors are inexpensive and the sensors can be operated on-site and on demand. Compared to commercial rapid bacteria tests (ATP and mycometer) that detect total bacterial based on enzyme activity or metabolites, the sensors according to the invention are more robust as they detect the bacteria cells without requiring a sample treatment process and without being temperature sensitive.

According to one embodiment the primary negatively charged, nanoparticulate sensing material is selected from the group of metal nanoparticles and graphene oxide. Advantageously, depending on the choice of the material, different behaviours in the distinction of living and dead bacteria can be achieved. The use of negatively charged graphene oxide (GO) allows the analysis of living versus dead bacteria at lower bacteria levels.

According to another embodiment of the invention the positively charged, fluorescent sensing material is selected from the group of water soluble cationic conjugated polyelectrolyte (CCPE) and positively charged peptide/polymer labeled with fluorescence dye. Depending on the choice of the material and its overall positive charge and charge distribution the limit of detection (LOD) of the sensor can be easily tuned to a desired range.

According to a second aspect of the invention there is provided a method for detecting bacteria comprising the steps of (a) providing a system for detecting bacteria, comprising a primary negatively charged, nanoparticulate sensing material, a secondary positively charged, fluorescent sensing material that electrostatically attached to said primary negatively charged, nanoparticulate sensing material shows suppressed florescence and at least one illuminator; (b) adding a sample comprising bacteria cells in aqueous medium to the system; (c) providing light of at least one pre-specified wavelength $\lambda_i$ to excite at least said fluorescent sensing material; (d) detecting or measuring the fluorescence of said fluorescent sensing material at a second wavelength $\lambda_n$ after electrostatically attachment of fluorescent sensing material to the bacteria cells in said sample.

Advantageously the method allows detecting the presence of bacteria and measuring an overall bacteria count which is non-specific to the bacteria type. No enzymes which are temperature or pH sensitive need to be used in this rapid and robust analytical method. The method is suitable for on-site applications as it does not require a laboratory. By choice of the sensing materials the LOD of the analytical method can be tuned easily.

Definitions

The following words and terms used herein shall have the meaning indicated:

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

As used herein, the term "sensor" refers to a device that detects or measures a property of a sample, such as the bacteria cell content, and records, indicates or otherwise responds to it.

As used herein, the term "nanoparticulate materials" or "nanomaterials" refers to materials that comprise particles of at least one nanometer dimension. Any microscopic particle which at least in one dimension has a size of less than about 100 nanometers (nm) may be a nanoparticulate material or nanomaterial, such as for instance a graphene oxide (GO) sheet with a thickness of less than about 100 nm.

As used herein, the term "nano" refers to refers to a microscopic dimension of less than 100 nanometers (nm).

As used herein, the term "fluorescent material" may refer to a material which exhibits fluorescence. Fluorescence is defined as the emission of light (or other electromagnetic radiation) by a material when stimulated by the absorption of radiation or of a subatomic particle, or the so emitted light depending on the context.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Unless specified otherwise, the terms "comprising" and "comprise", and grammatical variants thereof, are intended to represent "open" or "inclusive" language such that they include recited elements but also permit inclusion of additional, not recited elements. The terms "comprising" and "comprise" always include their meaning "consisting of" and "consist of" without being limited thereto.

The word "substantially" does not exclude "completely" e.g. a composition which is "substantially not leaking" may be completely tight without any leakage. Where necessary, the word "substantially" may be omitted from the definition of the invention.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and sub generic groupings falling within the generic disclosure also form part of the disclosure. This includes the generic description of the embodiments with a proviso or negative limitation removing any subject matter from the genus, regardless of whether or not the excised material is specifically recited herein.

DETAILED DISCLOSURE OF EMBODIMENTS

Non-limiting embodiments of the invention will be further described in greater detail by reference to specific examples, which should not be construed as in any way limiting the scope of the invention.

According to a first aspect of the invention an optical sensor that detects bacteria cells is provided (see FIG. 12) comprising (a) a primary negatively charged, nanoparticulate sensing material; (b) a secondary positively charged, fluorescent sensing material; (c) a housing; and (d) at least one illuminator; wherein said housing contains said primary negatively charged, nanoparticulate sensing material, said secondary positively charged, fluorescent sensing material and a sample potentially comprising bacteria in aqueous medium, wherein said illuminator provides light of at least one pre-specified wavelength $\lambda_i$ to excite at least said secondary positively charged, fluorescent material, wherein said secondary positively charged, fluorescent material electrostatically attached to bacteria cells provides at least one fluorescent response at a second different wavelength $\lambda_n$, wherein both i and n are integers, wherein said negatively charged, nanoparticulate sensing material electrostatically attached to said fluorescent material suppresses fluorescing of said fluorescent material at said second wavelength $\lambda_n$; and wherein said housing permits illumination of the contents of said housing by said illuminator and wherein said housing further permits the detection of a fluorescent response at said second wavelength $\lambda_n$.

The sensor detects bacteria. The detector may detect the presence of bacteria or detect the overall amount of bacteria (total bacteria count). In one embodiment the total bacteria count of all bacteria that have a negatively charged surface due to lipopolysaccharides or teichoic acids on the cell wall is detected. The sensor may detect gram positive and gram negative bacteria. They may be selected from the group of *Escherichia coli* (e.g. *Escherichia Coli*), *Salmonella* (e.g. *Salmonella typhimurium*), *Shigella* (e.g. *Shigella flexneri*), *listeria* (e.g. *Listeria monocytogenes*), *Staphylococcus* (e.g. *Staphylococcus aureus*), *Legionella* (e.g. *Legionella pneumophila*) and *Streptococcus* (e.g. *Streptococcus suis*), but they are not limited to these bacteria.

The primary sensing material is negatively charged. It may comprise nanoparticles. It may comprise microparticles with one dimension being in the nanomaterial range. The nanoparticles, especially the metal nanoparticles, may have an average size of about 1 to 100 nm, preferably about 3 to 50 nm and more preferably about 5 to 20 nm and most preferably about 7 to 18 nm. Other average sizes that can be mentioned are about 7, 13, 25, 60, 75 nm. The microparticles with at least one nanometer dimension, especially the GO particles, may have an average size of about 0.1 to 100 µm, preferably about 0.1 to 50 µm and more preferably about 0.1 to 20 µm and most preferably about 0.1 to 1 µm. Other average sizes that can be mentioned are about 2, 5, 13, 25, 60, 75 µm.

The material may be selected from the group of metal nanoparticles and graphene oxide. The graphene oxide may be in nanoparticulate form referring to the thickness of the graphene oxide sheets. Accordingly, the graphene oxide sheets may have length of about 0.1 to 100 µm, preferably about 0.1 to 50 µm and more preferably about 0.1 to 20 µm and most preferably about 0.1 to 1 µm. Other average sizes that can be mentioned are about 2, 5, 13, 25, 60, 75 µm. The thickness of the sheets may be in the range of 0.05 to 7 nm, preferably 0.5 to 2 nm, most preferably 0.1 to 1.5 nm. Thickness that can be mentioned includes 0.07, 0.2, 1, 3 and 5 nm. The particles, especially the metal particles may be of substantially spherical shape. The particles may also be substantially composed of nanorods or elliptical particles. The metal nanoparticles may be chosen from metal particles wherein the metal is selected from noble metals such as for instance gold and silver. To create negative charge on the metal particle it may be decorated with a negatively charged molecule. Such decoration can be achieved by hydrophobic interaction, ionic interaction or a covalent bond (conjugation). The molecule may preferably have a uniform negative charge. Preferably this molecule further protects the metal particles from aggregation induced by salt that may be present in bacteria samples. The conjugated molecule may be an oligonucleotide, such as a DNA or RNA strain. The oligonucleotide may be hybridized to form a double strain (ds). dsDNA or RNA may be particularly mentioned. The oligonucleotide may consist of 13 to 25 nucleotides. The dsDNA may have 5 to 50 base pairs, 10 to 20 base pairs may be particularly mentioned. Other suitable numbers of base pairs include 15, 17, 19, 21, 23, 32 or 43. The negative charge may result from the phosphate backbone of these molecules and is introduced to the metal nanoparticle. The DNA base sequence may therefore be unspecific, if the number of base pairs is chosen. The particle may be coated with other biomolecules to prevent aggregation in salt solutions. A metal particle that is conjugated with dsDNA may be particularly mentioned as primary sensing material.

The primary sensing material may also be a graphene oxide. The graphene oxide (GO) may not require any further surface modification to create negative charges, because GO has inherent negative charge from carboxylic acid and hydroxyl groups on its surface. However, in certain embodiments the graphene oxide may be further decorated with other negatively charged molecules, although this may not be necessary to achieve the effects of the invention. The GO may be composed substantially of a single layered two-dimensional hexagonal pattern $sp^2$-bonded carbon atoms and the edges of nanoparticles may contain functional exogenous oxygen bearing groups such as hydroxyl, carbonyl, carboxylic and epoxy group. The GO may be easily dispersed in water. The GO may have been synthesized based on the Hummers method, in which graphite is oxidized by a solution of potassium permanganate in sulfuric acid.

The concentration of the primary sensing material in the aqueous medium of the sensor can be varied depending on the material used. Metal nanoparticles may be used in nanomolar concentrations, such as about to 0.05 to 100 nM, or about 0.25 to 50 nM, or about 0.5 to 10 nM. Particular molar concentrations that can be mentioned include 0.3 nM, 1 nM, 2 nM, 5 nM, 10 nM, 25 nM. GO may be used in low concentrations in the aqueous medium of the sensor, such as about to 0.001 to 0.2 mg/mL, or about 0.005 to 0.1 mg/mL, or about 0.01 to 0.08 mg/mL. Particular concentrations that can be mentioned include 0.003 mg/mL, 0.007 mg/mL, 0.09 mg/mL or 0.15 mg/mL.

Preferably the primary sensing material is used in a buffered solution within the aqueous medium of the sensor. Typical buffers can be used, such as PBS buffer. The aqueous medium may substantially be water and an optional buffer. The pH may be chosen in the range of 4 to 9, preferably 5 to 8 and most preferably 5.5 to 7. PH values that can be particularly mentioned include 4.5, 5.3, 6.5 and 6.7.

The secondary positively charged, fluorescent sensing material may be selected from the group of cationic conjugated polyelectrolyte (CCPE) and positively charged peptide/polymer labeled with fluorescence dye or may show fluorescence. The secondary positively charged, fluorescent sensing binds electrostatically to the primary negatively charged sensing material, but preferably binds to bacteria in a competitive electrostatically binding. The preferred binding may be an unselective electrostatic binding to the negatively charged bacteria cell surface of various bacteria types.

The CCPE may be selected from π-conjugated polymers comprising side chains with cationic groups. Then π-conjugated polymer may be selected from the group of in each case cationic polythiophenes, poly(p-phenylene)s, poly(fluorene)s, poly(phenylene ethynylene)s, poly(fluorine ethynylenes)s, poly(phenylene vinylene)s, poly(fluorine vinylene)s and copolymers comprising these polymers. The cationic group may be selected from the group of quaternary ammonium, biguanidine, phosphonium, guanidine, sulfonium, or pyridinium groups; preferably they may be quarternary ammonium and pyridinium. Poly[(2,5-bis(2-(N,N-diethylammonium bromide ethoxy)-1,4-phenylene)-alt-1,4-phenylene] and poly[(9,9-di(3,3'-N,N'-trimethylammonium)propylfluorenyl-2,7-diyl)-alt-(1,4-phenylene)]diiodide salt-end capped with DMP may be mentioned as examples of CCPEs. The CCPE may have a weight average molecular weight ($M_w$) of about 250 to 100,000, preferably about 500 to 10,000, more preferably 700 to 1,500. Preferably the CCPE is water soluble.

The positively charged peptide labelled with fluorescence dye may comprise 5 to 100 amino acids in the peptide part. It may comprise 7 to 15 amino acids. 8, 9, 10, 11, 12, 13, 14, 25 or 50 amino acids may be particularly mentioned. It may be rich in histidine, lysine, arginine or mixtures thereof. In case a positive charged polymer is used, it may have the same $M_w$ and cationic groups as the above described CCPE.

The positively charged polymer may show fluorescence. Examples for such positively charged, fluorescent polymers include, without being limited thereto: Poly[(2,5-bis(2-(N,N-diethylammonium bromide ethoxy)-1,4-phenylene)-alt-1,4-phenylene], poly[(9-(6-N,N,N-trimethylammonium)hexyl-9'-(6-N,Ndiisopropylamine) hexyl)fluorenyldivinylene-alt-co-1,4-phenylene bromide], and poly[9,9-bis((6-N,N,N-trimethylammonium)-hexyl)fluorene-alt-co-2,1,3-benzoxadiazole dibromide].

The peptide or polymer may be labelled with a florescence dye. The fluorescent dye may be selected from the group of Abz (Anthranilyl, 2-Aminobenzoyl), N-Me-Abz (N-Methyl-anthranilyl, N-Methyl-2-Aminobenzoyl), FITC (Fluorescein isothiocyanate), 5-FAM (5-carboxyfluorescein), 6-FAM (6-Carboxyfluorescein), TAMRA (Carboxytetramethyl rhodamine), Mca (7-Methoxycoumarinyl-4-acetyl), AMCA/Amc (Aminomethylcoumarin Acetate), Dansyl (5-(Dimethylamino)naphthalene-1-sulfonyl), EDANS (5-[(2-Aminoethyl)amino]naphthalene-1-sulfonic acid), Atto (Atto465, Atto488, Atto495, Atto550, Atto647), Cy3 (1-(5-carboxypentyl)-3,3-dimethyl-2-((1E,3E)-3-(1,3,3-trimethylindolin-2-ylidene)prop-1-en-1-yl)-3H-indol-1-ium chloride), Cy5 (1-(5-carboxypentyl)-3,3-dimethyl-2-((1E,3E,5E)-5-(1,3,3-trimethylindolin-2-ylidene)penta-1,3-dienyl)-3H-indolium chloride), Alexa Fluor (Alexa Fluor 647, Alexa488, Alexa532, Alexa546, Alexa594, Alexa633, Alexa647), Bodipy, Dylight (DyLight 488, DyLight 550), Trp (Tryptophan), Lucifer Yellow ((ethylene diamine) 6-Amino-2-(2-amino-ethyl)-1,3-dioxo-2,3-dihydro-1H-benzo[de]isoquinoline-5,8-disulfonic acid) and mixtures thereof.

Depending of the choice of the fluorescent dye the sensor may also be used for applications of the time-resolved fluorescence (TRF) phenomenon.

The secondary sensing material may be used in low concentrations in the aqueous medium of the sensor, such as about to 0.0005 to 0.1 mg/mL, or about 0.001 to 0.05 mg/mL, or about 0.0007 to 0.05 mg/mL. Particular concentrations that can be mentioned include 0.002 mg/mL, 0.004 mg/mL, 0.09 mg/mL or 0.15 mg/mL.

The illuminator may be a light source that produces light of at least one pre-specified wavelength $\lambda_i$ that is able to excite the secondary fluorescent sensing material. $\lambda_i$ may be chosen according to the fluorescent sensing material. It may be in the range of about 300 to 600 nm. The wavelength may be about 334, 410, 470, 520 or 630 nm. The illuminator may be in the form of a light emitting diode (LED) or any other light source commonly used in fluorescence spectrometers.

The negatively charged, nanoparticulate sensing material and the positively charged, fluorescent sensing material are in an aqueous medium optionally further comprising said bacteria cells. The aqueous medium may comprise additives besides water. The aqueous medium may be water which optionally comprises a buffer. The bacteria may be living bacteria or dead bacteria that are detected by the sensor. The bacteria may be present or absent (blank) depending on the sample. The bacteria may be those of a sample that is analysed for the presence of the bacteria or for the amount of bacteria.

The fluorescing material electrostatically attached to bacteria cells provides at least one fluorescent response at a second wavelength $\lambda_n$. $\lambda_n$ may be an emitting wavelength of the secondary fluorescent sensing material. $\lambda_n$ may be pre-determined by choice of the fluorescent sensing material. It may be in the range of 300 to 1400 nm. In one embodiment $\lambda_n$ may be in the near-infrared (NIR) light range (600 nm to 1400 nm). The wavelength $\lambda_n$ may be about 410, 520 or 590 nm.

The negatively charged, nanoparticulate sensing material electrostatically attached to the positively charged fluorescent material suppresses fluorescing of said fluorescent material at said second wavelength $\lambda_n$. It is a fluorescence quencher. The sensing principle of the sensor is therefore based on competitive electrostatically interaction between the positively charged fluorescent sensing material with either the bacteria cells or the negatively charged sensing material. The negatively charged material, e.g. the dsDNA-AuNPs or GO, may be therefore used as fluorescence quencher to construct a fluorimetric competition assay together with the positively charged florescent material. The sensing principle of the sensor is based on the fluorescence resonance energy transfer (FRET) in the quenching of the positively charged fluorescent sensing material. In case of using dsDNA-AuNPs or GO, the naturally occurring negative charges (from DNA backbone and the COO—/O— on GO surface) are used for electrostatic binding/attachment, and the AuNPs and GO do not require specifically tailored polymer structure for surface modification. The sequence of the DNA can therefore be random.

The sensor further comprises a housing containing at least the primary negatively charged, nanoparticulate sensing material, the secondary positively charged, fluorescent sensing material and optionally the bacteria in aqueous medium, wherein said housing permits illumination of the contents of said housing by the illuminator and wherein the housing further permits the detection of a fluorescent response at a second wavelength $\lambda_n$. The housing can be chosen from typical housings used in an apparatus for performing a fluorescence assay. The housing permits illumination of its contents by the illuminator. The housing further permits addition of a sample potentially comprising bacteria via an opening. It may be made of any transparent or black material. It may be a well of a well plate to allow high-throughput sensing of multiple samples. A 96-well plate may be particularly mentioned as a suitable form of multiple housings for high-throughput analysis in standard systems.

According to a second aspect of the invention a method for detecting bacteria comprising the steps of (a) providing a system comprising a primary negatively charged, nanoparticulate sensing material; a secondary positively charged, fluorescent sensing material that electrostatically attached to said primary negatively charged, nanoparticulate sensing material shows suppressed florescence; and at least one illuminator; (b) adding a sample comprising bacteria cells in aqueous medium to the system; (c) providing light of at least one pre-specified wavelength $\lambda_i$ to excite at least said fluorescent sensing material; (d) detecting or measuring the fluorescence of said fluorescent sensing material at a second wavelength $\lambda_n$ after electrostatically attachment of fluorescent sensing material to the bacteria cells in said sample.

The method may be used for the unspecific, non-selective detection of the presence and amount of bacteria (total bacteria count) in a sample. The method may be used for high-throughput analysis of bacteria from a larger amount of samples using standard assay technologies, preferably involving standardized well plates and microplate readers.

The sensing materials and illuminator of the system are those substantially described above for the sensor of the first aspect of the invention. The system may therefore comprise the sensor of the first aspect of the invention. The system may further include the housing or several such housings as described above and a fluorescence detector that can measure fluorescence at the wavelength of $\lambda_n$. The housing may be filled with an aqueous medium, preferably a buffered medium, wherein the sensing materials are dissolved. The illuminator can excite the secondary sensing material by emitting light at a wavelength of $\lambda_i$. The assembled system may be provided in step (a) of the method according to the invention. The complete system may be provided before or after adding the sample in step (b). It is therefore possible to add sensing materials after the sample comprising bacteria cells is added to the system components, especially the aqueous medium. For instance the primary sensing material may be provided first, then the bacteria sample is added and finally the secondary sensing material is added. The detection of florescence may be performed using a commercially available microplate reader as another component comprised in the system. In this type of apparatus, a first optical system (excitation system including the illuminator) illuminates the sample using at least one specific wavelength $\lambda_i$ (selected by an optical filter, or a monochromator). As a result of the illumination, the secondary sensing material emits light at a wavelength of $\lambda_n$ (it fluoresces) and a second optical system (emission system) collects the emitted light, separates it from the excitation light (using a filter or monochromator system), and measures the signal using a light detector such as a photomultiplier tube (PMT). The sensor of the first aspect of the invention may comprise parts of such apparatus.

According to step (b) a sample comprising bacteria cells is added to the aqueous medium of the system. As described above, this step (b) can be done before, during or after providing the system of step (a). The sample may also be in aqueous medium and fully miscible with the aqueous medium of the system. The volume of the bacteria sample can be less or more than the volume of the aqueous medium. The volumes may be in the range of 1:2 to 2:1, preferably 1.5:1 to 1:1.5. The volume of the aqueous medium of the system may be added together with the sensing materials in separate amounts to the housing. For instance about 50 to 70% of the volume may be added before adding the sample and about 30 to 50% thereafter. All aqueous media may be buffered. It may be preferred to add a buffer with the first adding of medium to the housing of the system.

According to step (c) light of at least one pre-specified wavelength $\lambda_i$ to excite at least the fluorescent sensing material is provided. The light may be provided by the illuminator. The wavelength of the light can be chosen as described above for the sensor according to the invention depending on the fluorescent moiety employed.

According to step (d) the fluorescence of said fluorescent sensing material at a second wavelength $\lambda_n$ after electrostatically attachment of fluorescent sensing material to the bacteria cells in said sample is measured. The measurement can make use of a light detector such as a photomultiplier tube without being limited to such type of detector. The detector can either be single-channeled or multi-channeled. The single-channeled detector can only detect the intensity of one wavelength at a time, while the multi-channeled detects the intensity of all wavelengths simultaneously making an emission monochromator or filter unnecessary. The detector may be placed substantially perpendicular to the incident light beam of the illuminator. The detected fluorescence using a bacteria sample ($F_{sample}$) may be recorded for comparison in fluorescence increase with the fluorescence of a blank sample.

After completion of the steps (a) to (d) of the method of the invention the following steps (e) to (h) may be performed. Those steps can also be comprised in the method of the invention: (e) providing the said system of step (a), comprising the primary negatively charged, nanoparticulate sensing material; the secondary positively charged, fluorescent sensing material; and the illuminator; (f) adding a blank sample comprising no bacteria cells in aqueous medium to the system; (g) providing light of at least one pre-specified wavelength $\lambda_i$ to excite at least said fluorescent sensing material; (h) detecting or measuring the fluorescence of said fluorescent sensing material at a second wavelength $\lambda_n$. The measured fluorescence using a blank sample ($F_{blank}$) can be used to calculate a fluorescence increase according to formula 1:

$$\% \text{ Fluorescence increase} = \frac{(F_{sample} - F_{blank})}{F_{blank}} \times 100\% \qquad [\text{Formula 1}]$$

The fluorescence increase may be used to detect the presence of the bacteria cells or determine the overall amount of bacteria cells. The method may make use of samples of known bacteria cell count to determine florescence increases using formula (I) after fluorescence measurement using the method of the invention. In this way the system can be calibrated and samples of unknown bacteria count quantified for their bacteria amounts after comparison to a calibration curve of the system obtained using the method of the invention with known standard samples.

The system of the method of the invention may further comprise an analysis unit that changes its status when the fluorescence detector signal exceeds a pre-set fluorescence value to indicate the presence of a certain threshold concentration of total bacteria cells.

The sensing principle of the method according to the invention is based on the competitive binding of the negatively charged bacteria cell surfaces and the negatively, charged nanoparticulate materials with the positively charged, fluorescent materials. An electrostatic binding of the positively charged florescent material with the bacteria cells without any substantial florescence loss is important. To detect all negatively charged bacteria this electrostatic binding may be non-selective to the bacteria type. The fluorescent material may preferably bind/attach to the bacteria and not the negatively charged sensing material. In order to achieve a complete binding of the florescent sensing material with the bacteria a certain reaction time may be allowed. Typically at least 2 minutes and up to 30 minutes may be suitable. Times of 5, 10, 15 or 20 minutes may be further mentioned. This time period starts at the time that the bacteria and the all the sensing materials are present in the aqueous medium and ends with the measurement of the fluorescence.

Depending on the charge density of the secondary positively charged, fluorescent sensing material the limit of detection (LOD) of the method to detect the bacteria may vary. By choice of said material a pre-set fluorescence increase value that is identical to a desired detection limit of bacteria can be adjusted. The adjustment may be achieved by using different ratios of cationic amino acids in the peptide chain of the peptide conjugated to a fluorescent dye. The method according to the invention may further be used to detect gram positive and gram negative bacteria. They may be selected from the group of *Escherichia coli* (*Escherichia Coli*), *Salmonella* (*Salmonella typhimurium*), *Shigella* (*Shigella flexnen*), *Listeria* (*Listeria monocytogenes*), *staphylococcus* (*Staphylococcus aureus*), *Legionella* (*Legionella pneumophila*), *Streptococcus* (*Streptococcus suis*), but is not limited to these bacteria. Bacteria cells that comprise *E. coli* or *S. aureus* strains may be particularly mentioned. However, the method according to the invention may not be selective to a specific bacteria type, but may be used to detect the total amount of a variety of bacteria cells at the same time.

The method of the invention may be used to distinguish between living and dead bacteria cells. The sensitivity of the method according to the invention towards living bacteria is significantly higher than towards dead bacteria. The method may even be selective for living bacteria. The use of graphene oxide as negatively charged sensing material may be preferred to achieve a high selectivity for living bacteria.

EXAMPLES

The sensors and the methods according to the invention are characterized in the following examples which in no way limit the invention to the scope of the examples.

Example 1

Fluorimetric competition assay involving positively charged luminescent materials and negatively charged AuNPs for total bacteria counting and differentiation of live/dead bacteria Mechanism:

This sensor is based on a competitive binding of positively charged luminescent materials with either the negatively charged bacteria cells or negatively charged dsDNA-AuNPs (FIG. 1). When there are no bacteria in the sample, positively charged luminescent materials mostly bind to negatively charged dsDNA-AuNPs through electrostatic interaction, and their fluorescence is quenched by AuNPs through fluorescence resonance energy transfer (FRET). When bacteria are present in the sample, the negatively charged bacteria cells compete with negatively charged dsDNA-AuNPs to bind the positively charged luminescent materials that limits the binding of the luminescent materials to dsDNA-AuNPs quencher. As a result, the fluorescence intensity remains high, higher than the quenched state when there is no bacteria present ($F_{blank}$). The difference in the fluorescence intensity between that with bacteria sample ($F_{sample}$) (non-quenched state) and the quenched state without bacteria ($F_{blank}$) can be calculated as % fluorescence increase, which is proportionally related to the amount of bacteria in the sample. The calculation is as shown in formula 1:

$$\% \text{ Fluorescence increase} = \frac{(F_{sample} - F_{blank})}{F_{blank}} \times 100\% \quad \text{[Formula 1]}$$

Sensor Components and Their Preparation Methods:

Two assay components are included in this assay, namely (1) negatively charged dsDNA AuNPs, and (2) positively charged luminescent materials. To create negative charge on AuNPs, dsDNA is chosen, because dsDNA has uniform negative charge from its phosphate backbone, and dsDNA coating on AuNPs has improved AuNPs stability against aggregation induced by salt that may present in bacteria sample. To prepare dsDNA-AuNPs, dsDNA (random sequence, 19 bp) is conjugated to spherical AuNPs (diameter 13 nm) through thiol linkage according to the protocol of Lukman, et al. (ACS Appl. Mater. Interfaces 2013, 5, 12725). Meanwhile, positively charged luminescent materials can be selected from water soluble cationic conjugated polyelectrolyte (CCPE) such as poly[(2,5-bis(2-(N,N-diethylammonium bromide ethoxy)-1,4-phenylene)-alt-1,4-phenylene], or other positively charged peptide/polymer labelled with fluorescence dye. The positive charge density in the peptide/polymer can be selected to tune the limit of detection of the fluorimetric assay.

CCPE poly[(2,5-bis(2-(N,N-diethylammonium bromide ethoxy)-1,4-phenylene)-alt-1,4-phenylene]was purchased from Sigma Aldrich (product code 678074). CTXI-FITC was custom synthesized by GL Biochem (China), the bacteria samples were *E. coli* ATCC 25922 and *S. aureus* ATCC 6538 cultured by the Institute of Materials Research and Engineering (IMRE) in Singapore on natural agar plate and dispersed in saline solution (0.9% NaCl).

Preparation of dsDNA-AuNPs According to Lukman et al.:

Thiolated single stranded DNA (ssDNA, i.e. the sense strand) was activated with tris(2-carboxyethyl)phosphine (TCEP, 10 molar excess) and stirred for 10 min. The final solution was centrifuged, with a Sigma-Aldrich microcentrifugal filter device, YM-3 (NMWCO 3 kDa), to remove TCEP before conjugation to AuNPs. The TCEP-activated DNA was mixed with AuNPs at the desired molar ratio (100:1) and incubated for 5 min. The pH of solution was then lowered to 3 and salt concentration was increased to 30 mM by adding HCl and NaCl, respectively. After 20 min incubation, NaOH was added to return the pH to a neutral range. The ssDNA-AuNPs conjugates were then annealed with its complimentary DNA strands at 90° C. for 5 min and let to cool down to room temperature (RT).]

Sensor Assay:

An optical sensor assay was performed in a 96-well plate (Costar). In each well, 40 µL of 2.5 nM dsDNA-AuNPs in PBS buffer was mixed with 50 µL of bacteria sample. Then, 10 µL of CCPE (0.01 mg/mL) was added into the mixture. For standard of the quenched state, a well was prepared where blank sample was added instead of bacteria sample. After 15 minutes incubation, the fluorescence intensity in each well ($F_{sample}$) was measured by using a microplate reader (TECAN, Infinite M200) with an included built in Xenon lamp and fluorescence monochromator. The difference in the fluorescence intensity of $F_{sample}$ from the quenched state of the blank sample ($F_{blank}$) was calculated.

Sensor Assay Results (Total Bacteria Counting):

A competition sensor assay to measure Gram negative bacteria, e.g. *E. coli*, and Gram positive bacteria, e.g. *S. aureus* samples, by using either CCPE or a positively charged peptide has been performed. FIG. 2 shows the result using CCPE. Particularly, an increase in the fluorescence of CCPE is observed when bacteria present in the sample. The percentage of fluorescence increase is proportionally related to the *E. coli* and *S. aureus* concentration. Fluorescence increase can be observed even when the bacteria concentration is as low as 10 cfu/mL.

FIG. 3 shows the result using a peptide labelled with fluorophores to replace CCPE. The peptide is a short peptide with sequence of EKAHDGGRYYRA (SEQ ID NO: 1) labelled with fluorescein (FITC). The peptide has few positive charge moieties from the side chains of Lysine (K), Histidine (H), and Arginine (R). However, the positive charge density of the peptide is lesser than the positive charge density of CCPE. From the fluorimetric competition assay by using peptide-FITC and dsDNA-AuNPs, increase in fluorescence can only be observed when the *E. coli* concentration is higher than $10^5$ cfu/mL. The LOD of this system is higher than the LOD obtained from using CCPE and dsDNA-AuNPs. This result shows that the LOD of the sensor assay can be tuned by using luminescent materials with different type of positive charge density.

Sensor Assay Results (Differentiation of Live and Dead Bacteria):

The effect of dead *E. coli* cells (autoclaved *E. coli*) to the fluorimetric response, using the CCPE sensor was evaluated. Dead *E. coli* cells may retain some negative charge, and their presence may cause some fluorescence increase. However, the increase in fluorescence caused by the dead cells is smaller than the increase caused by live *E. coli* cells when the bacteria concentration is higher than $10^5$ cfu/mL (FIG. 4). This result shows the ability of the fluorimetric competition assay using CCPE and dsDNA-AuNPs to differentiate live and dead cells at concentration higher than $10^5$ cfu/mL.

Example 2

Fluorimetric competition assay involving positively charged luminescent materials and negatively charged graphene oxide (GO) for total bacteria counting and differentiation of live and dead bacteria Mechanism:

This assay is based on competitive electrostatically interaction of positively charged luminescent materials with negatively charged bacteria cells and negatively charged GO (FIG. 5). When there are no bacteria in the sample, positively charged luminescent materials mostly bind to negatively charged GO, and the fluorescence intensity is quenched by GO through Fluorescence Resonance Energy Transfer (FRET). When bacteria present in the sample, the negatively charged bacteria cells compete with negatively charged GO to bind the positively charged luminescent materials. The luminescent materials bound on bacteria cells are not quenched by GO, and maintain their fluorescence intensity, resulting in a higher fluorescence intensity than the quenched state when there is no bacteria present ($F_{blank}$). The difference in the fluorescence intensity with the bacteria sample ($F_{sample}$) from the quenched state without bacteria ($F_{blank}$) can be calculated as % fluorescence increase, which indicates bacteria in the sample. The calculation is the same as in Example 1.

Sensor Components and Their Preparation Methods:

Two assay components are included in this assay, namely (1) negatively charged GO, and (2) positively charged luminescent materials. GO requires no further surface modification to get negative charge because GO has inherent negative charge from carboxylic acid and hydroxyl groups on its surface. Positively charged luminescent materials can be selected from water soluble cationic conjugated polyelectrolyte (CCPE) such as poly[(2,5-bis(2-(N,N-diethylammonium bromide ethoxy)-1,4-phenylene)-alt-1,4-phenylene], or other positively charged peptide/polymer labeled with fluorescence dye. The positive charge density in the peptide/polymer can be selected to tune the limit of detection of the fluorimetric assay.

GO was purchased from Sigma Aldrich (product code 763705), CTXI-FITC was custom synthesized by GL Biochem (China), the bacteria samples were *E. coli* ATCC 25922 and *S. aureus* ATCC 6538 cultured in IMRE on natural agar plate and dispersed in saline solution (0.9% NaCl).

Sensor Assay:

An optical sensor assay was performed in a 96-well plate (Costar). In each well, 30 µL of 0.067 mg/mL GO in PBS buffer was mixed with 50 µL of bacteria sample. Then, 20 µL of 0.01 mg/mL CCPE (or peptides) was added into the mixture. For standard of the quenched state, a well was prepared where blank bacteria sample was added instead of bacteria sample. After 15 minutes incubation, the fluorescence intensity in each well was measured by using a microplate reader (TECAN, Infinite M200). The difference in the fluorescence intensity of $F_{sample}$ from $F_{blank}$ was calculated as described above.

Sensor Assay Results (Total Bacteria Counting):

A competition sensor assay to measure Gram negative bacteria, e.g. *E. coli* and Gram positive bacteria, e.g. *S. aureus* samples has been performed. FIG. 6 shows the result using CCPE. It shows the increase in fluorescence spectrum of CCPE when bacteria present in the sample and the percentage of fluorescence increase is proportional to the *E. coli* and *S. aureus* concentration. Fluorescence increase can be observed even when the *E. coli* concentration is as low as 1 cfu/mL.

Furthermore, peptide (EKAHDGGRYYRA (SEQ ID NO: 1)) labeled with FITC was used to replace CCPE. FIG. 7 shows the result using a peptide labeled with fluorophores to replace CCPE. The peptide has few positive charge moieties from the side chains of Lysine (K), Histidine (H), and Arginine (R), but the positive charge density on the peptide is lesser than the positive charge density of CCPE. From the fluorimetric competition assay by using peptide-FITC and GO, increase in fluorescence can only be observed when the *E. coli* concentration is higher than $10^5$ cfu/mL. The LOD of this system is higher than the LOD obtained from using CCPE and GO. This result shows that the LOD of the sensor assay can be tuned by using luminescent materials with different positive charge density.

Sensor Assay Results (Differentiation of Live and Dead Bacteria):

The effect of dead *E. coli* cells (autoclaved *E. coli*) to the fluorimetric response using CCPE and GO as sensing materials was evaluated. Dead *E. coli* cells do not cause any fluorescence increase (FIG. 8). This result shows the ability of fluorimetric competition assay by using CCPE and GO to differentiate live and dead cells at any *E. coli* concentration.

Example 3

Interference of Coloration and Other Impurities

Ketchup, soy sauce, pulpy orange juice samples were tested. The microplate reader is TECAN, model Infinite M200. The microplate reader set up includes built-in Xenon lamp and fluorescence monochromator.

CCPE poly[(2,5-bis(2-(N,N-diethylammonium bromide ethoxy)-1,4-phenylene)-alt-1,4-phenylene] was purchased from Sigma Aldrich (product code 678074). PFBD poly[9, 9-bis((6-N,N,N-trimethylammonium)hexyl)fluorene-alt-co-2,1,3-benzoxadiazole dibromide was synthesized by Prof. Liu Bin's group in NUS. GO was purchased from Sigma Aldrich (product code 763705). Bacteria samples were *E. coli* ATCC 25922 and *S. aureus* ATCC 6538 cultured in IMRE on natural agar plate.]

When tested as received (no-dilution), these samples have auto-fluorescence background that masks the fluorescence signal of the luminescent sensing materials, cationic conductive polyelectrolyte CCPE-410 that emits at 410 nm (FIG. 9).

The auto-fluorescence background decreases when the samples are diluted (10 to 100 times, depending on the sample density). FIG. 10 shows the bacteria detection in a diluted juice sample (20 times dilution) by using graphene oxide as primary sensing material and CCPE-410 as secondary sensing material. The auto-fluorescence of the diluted juice is negligible and no mask over the fluorescence spectrum of CCPE-410. Furthermore, increase in fluorescence intensity can be observed when E. coli is spiked in the diluted juice.

Alternatively, to totally eliminate the interference of the food matrix, the sensor assay according to the invention can be developed in the Near Infra-Red (NIR) region that has significantly lower auto-fluorescence background from the food/beverage matrices (see auto-fluorescence comparison in different wavelength in FIG. 11). To develop the assay in NIR region, the currently used CCPE (emission at 410 nm) can be replaced by using positively charged luminescent materials that emit in NIR wavelength, for example: poly [9,9-bis((6-N,N,N-trimethylammonium)hexyl)fluorene-alt-co-2,1,3-benzoxadiazole dibromide] (PFBD) that emits at 630 nm.

The temperature and pH range depend on the sensing materials used in the sensors. The assays contain nanomaterials, i.e. dsDNA-AuNPs and GO, as the primary sensing materials, and luminescent materials, i.e. cationic conductive polyelectrolyte (CCPE), as the secondary sensing materials.

The sensor according to the invention shows a broader usage capability for food applications and other uses. The table below shows the pH and temperature stability of these sensing materials of the invention in comparison to sensing materials from other technologies for total bacteria count measurement (mainly enzymes). In general, the materials used in this technology are more robust and stable.

[Table 1] shows a comparison of the robustness of the sensing materials.

TABLE 1

| Technologies | Sensing materials | Temperature range | pH range |
|---|---|---|---|
| Invention | dsDNA-AuNPs | Up to 70° C. | 2-14 |
| | GO | Up to 200° C. | All pH |
| | CCPE | Up to 100-150° C. | 1-10 |
| ATP method | Luciferase | 20-35° C. | 6-8 |
| Bactiquant ® mycometer | Bacteria hydrolase | 18-35° C. | 6-8 |

The sensor according to the invention is designed for total bacteria count with detection limit of 1 cfu/mL. The examples show can meet the requirement of general total bacteria count in various industries (see Table 2).

[Table 2] shows a comparison of the robustness of the sensing materials.

TABLE 2

| | Bacteria testing required | | | |
|---|---|---|---|---|
| | Total bacteria count | | Specific bacteria detection | |
| Industry | Bacteria types | Sensitivity level | Bacteria types | Sensitivity level |
| Industrial water, e.g. cooling tower water | All (37° C., 24 h) | $10^5$ cfu/mL | Legionella | 10 cfu/mL |
| Public recreational water, such as swimming pool | All (37° C., 24 h) | 200 cfu/mL | E. coli | 1 cfu/100 mL |
| Drinking water | All (37° C., 48 h) | $10^5$ cfu/mL | E. coli | 1 cfu/250 mL |
| Marine ballast water discharge | All (37° C., 24 h) | 10 cfu/mL | E. coli | 2.5 cfu/mL |
| Food | All (37° C. 48 h) | $10^5$ cfu/mL | E. coli, Salmonella, Listeria | 1 cfu/25 g |

The examples show that the sensor is useful for total bacterial counting, based on charge interaction, and thus targets all type of bacteria. For a specific bacteria type, this sensor can be served as a platform technology, through further development (e.g. modifying the surface of the sensing materials with bio-affinity materials, aptamers, antibodies, etc.), new technology to target a specific bacteria can be delivered to meet the specific bacteria requirement.

Example 3 shows a potential for improvement in food analysis by using the sensor. Currently bacteria testing in food industries rely on bacteria plate count or PCR in laboratories. Food samples with proper statistical sampling procedure are collected and sent to laboratories in closed containers. Solid food samples are put into mechanical blender into homogenates, and re-suspended in buffer solution for inoculation. The inoculation may take 1 day or longer in agar plate followed by plate counting, or 12 hours to 1 day in liquid medium followed by PCR. Such cumbersome procedure may be avoided by used of the sensor according to the invention.

DESCRIPTION OF DRAWINGS

The accompanying drawings illustrate a disclosed embodiment or reaction scheme and serve to explain the principles of the disclosed embodiments. It is to be understood, however, that the drawings are designed for purposes of illustration of examples only, and not as a limitation of the invention.

In FIG. 4, CTW means Cooling Tower Water (water collected from cooling tower in Singapore). Bacteria spiked in and autoclaved CTW (to kill any live bacteria) were tested. The CTW is different from DI water used for other bacteria sample preparation as the CTW contains other impurities from the cooling tower such as dust, fine particles, ion species, etc.

INDUSTRIAL APPLICABILITY

Figure 1:
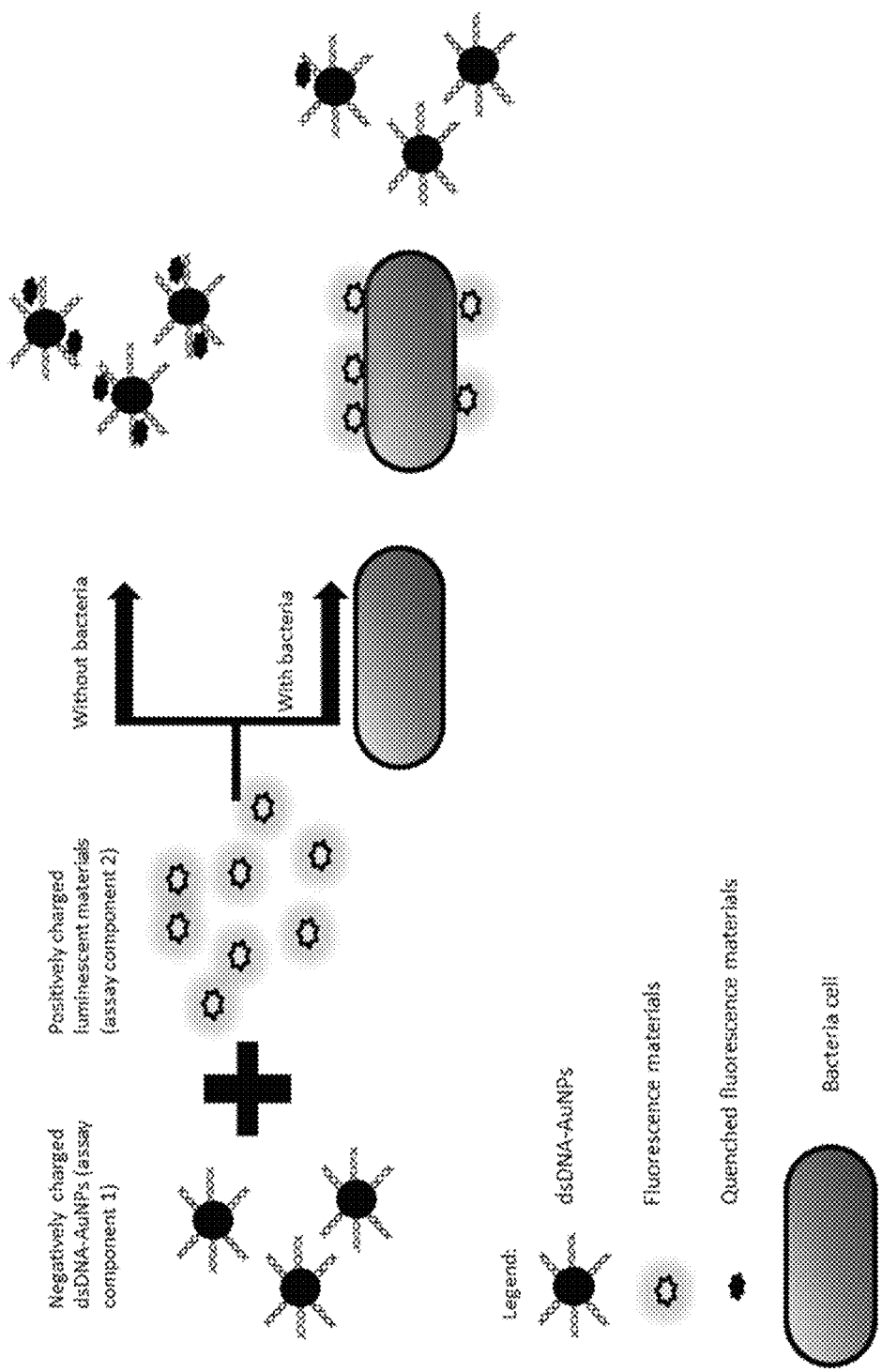
FIG. 1 shows a schematic illustration of the bacteria cell detection in a fluorimetric competition assay by using positively charged luminescent materials and negatively charged dsDNA-AuNPs.
Figure 2:
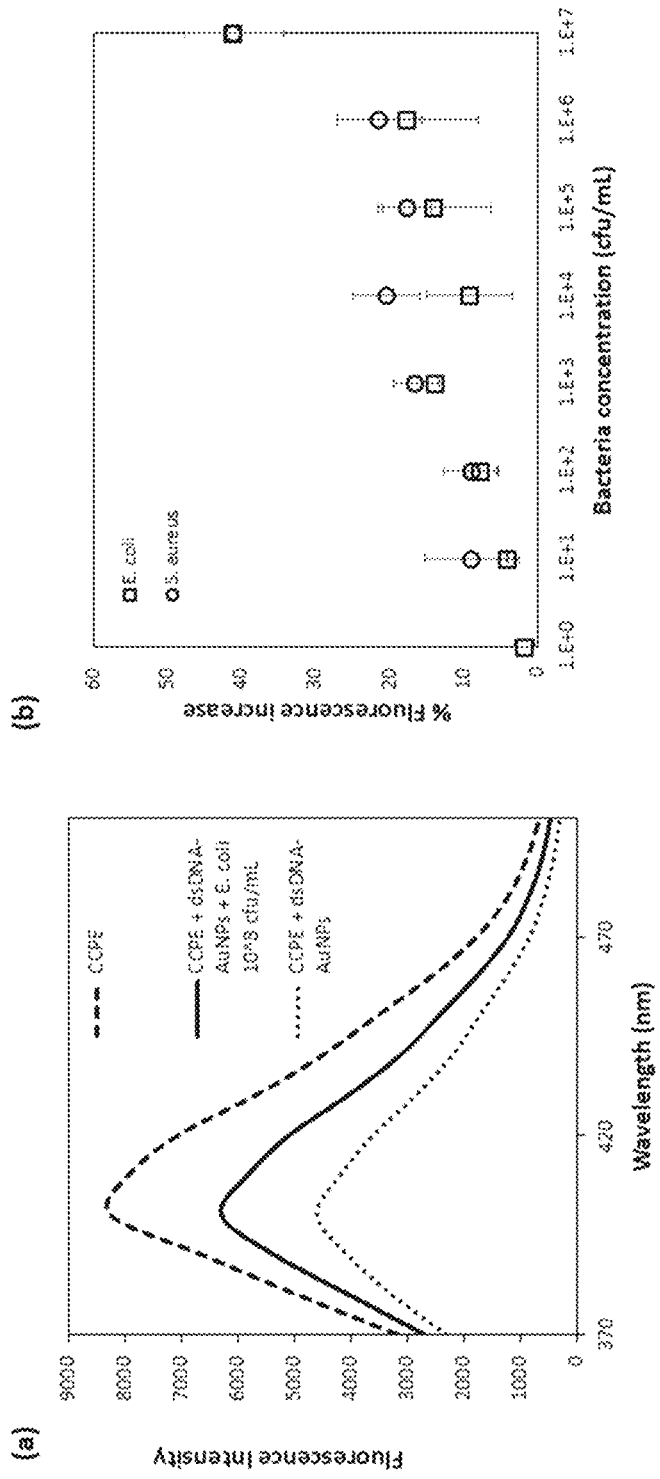
FIG. 2 shows (a) a fluorescence spectrum ($\lambda_{ex}$=334 nm) of CCPE before mixing with dsDNA-AuNPs and bacteria (initial, top line), after mixing with dsDNA-AuNPs without bacteria ($F_{blank}$, bottom line), and after mixing with dsDNA-AuNPs with E. coli sample ($F_{sample}$, middle line) and (b) the percentage of fluorescence increase from fluorimetric competition assay by using CCPE and dsDNA-AuNPs as a function of E. coli (square) and S. aureus concentration (circle).
Figure 3:
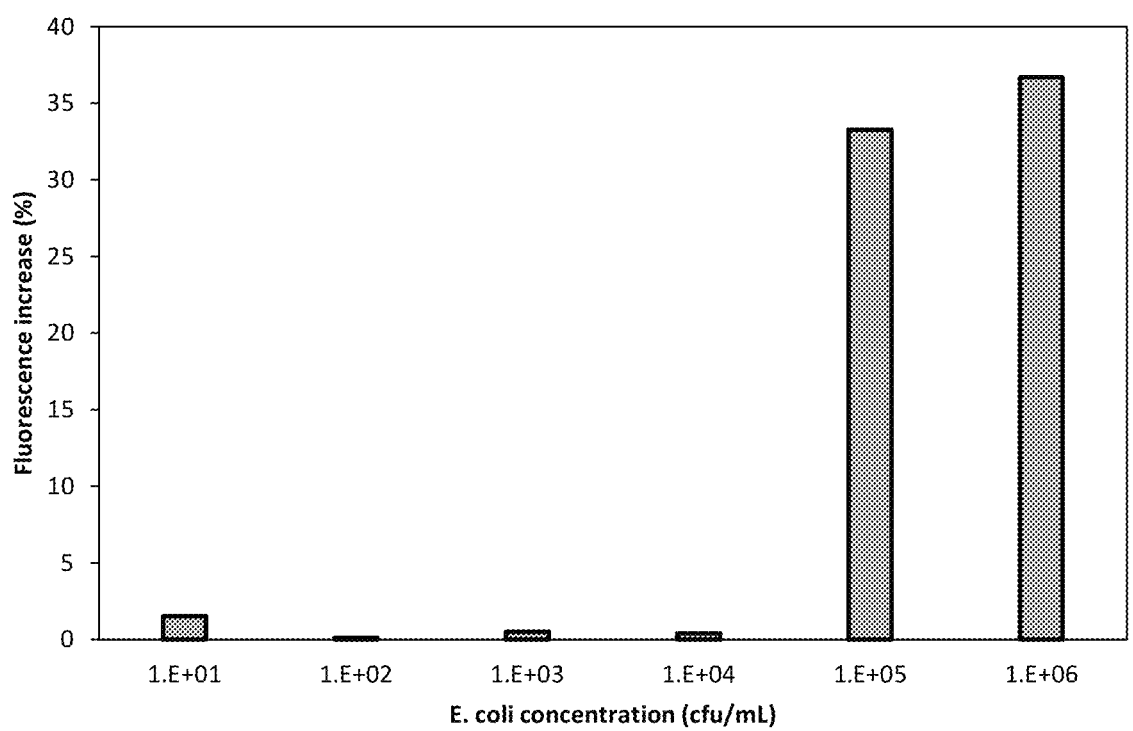
FIG. 3 shows the percentage of fluorescence increase from the fluorimetric competition assay by using peptide-FITC and dsDNA-AuNPs as a function of live E. coli concentration.
Figure 4:
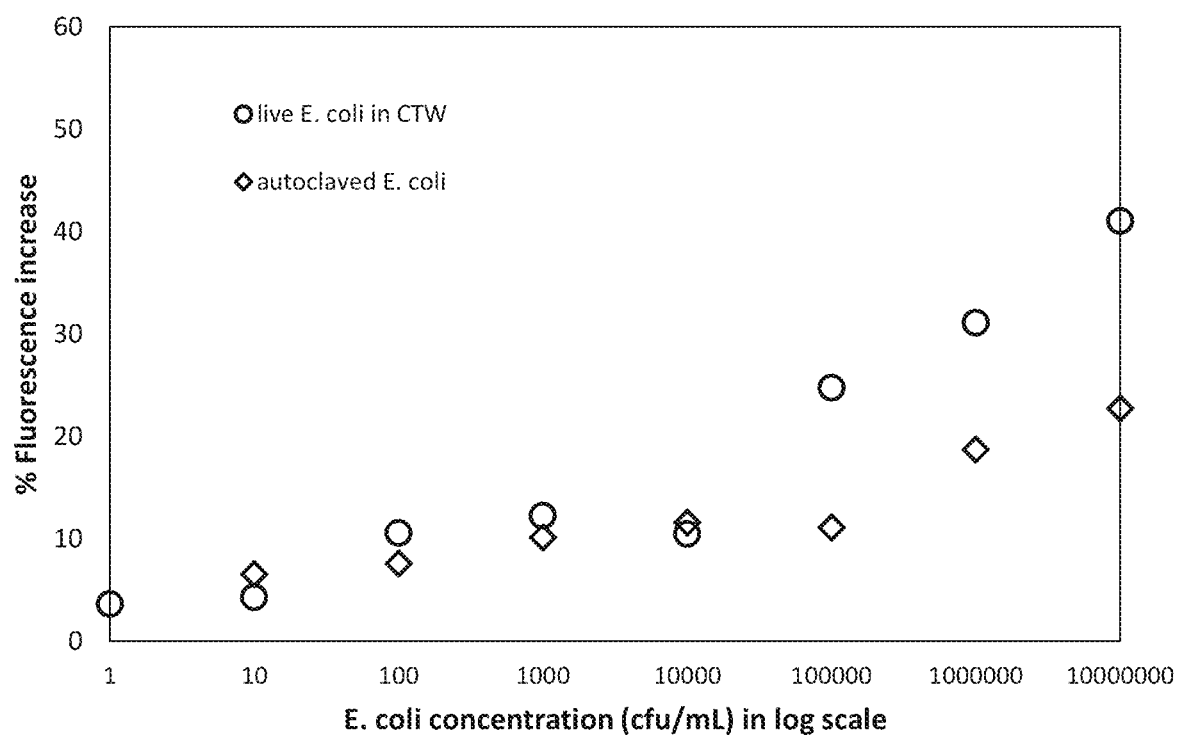
FIG. 4 shows the percentage of fluorescence increase from the fluorimetric competition assay by using CCPE and dsDNA-AuNPs as a function of the concentration of live E. coli (dots) and deadautoclaved E. coli (squares).
Figure 5:
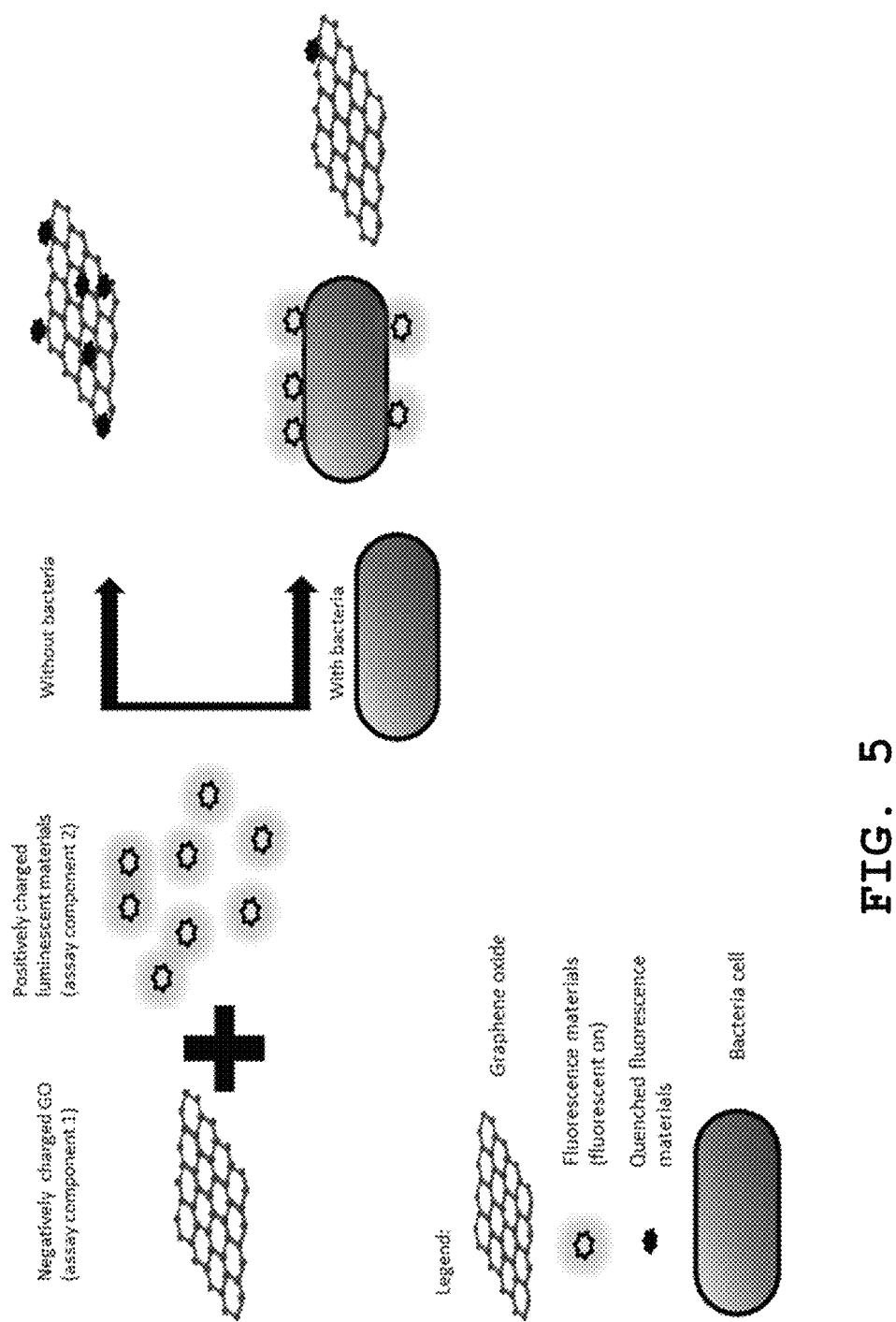
FIG. 5 shows a schematic illustration of the bacteria cell detection in a fluorimetric competition assay by using positively charged luminescent materials and negatively charged GO.
Figure 6:
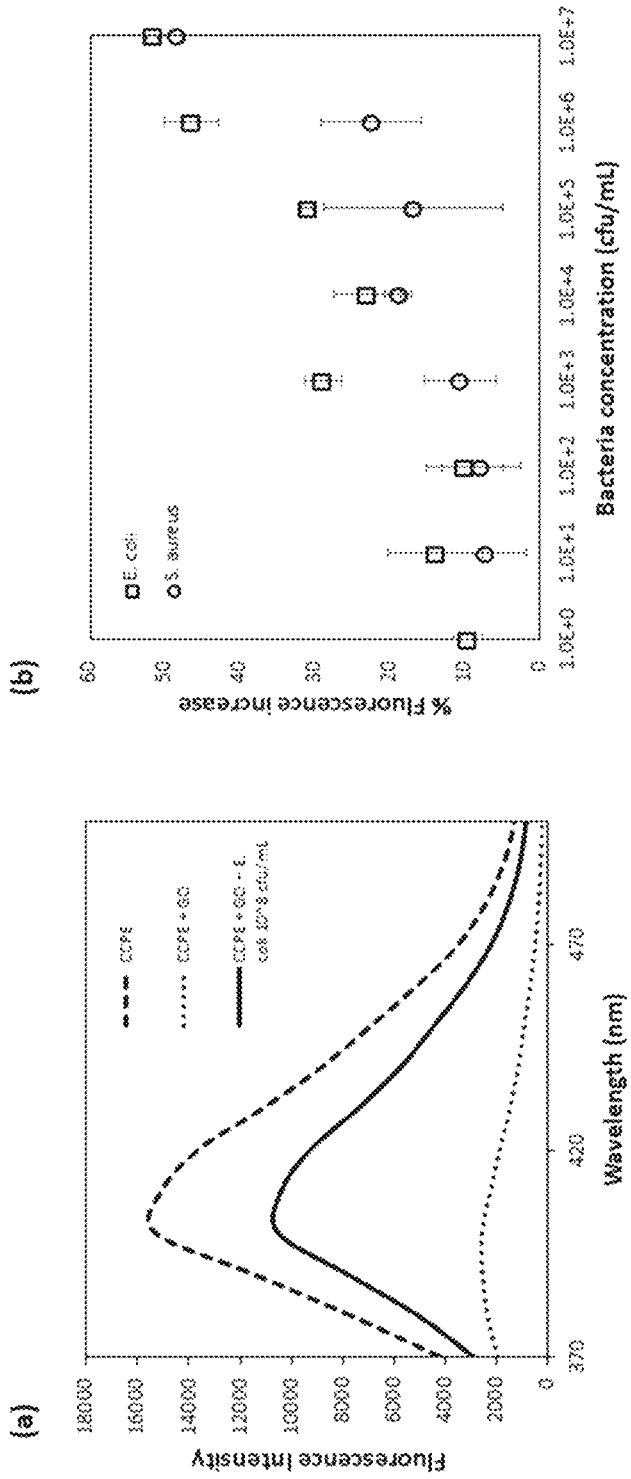
FIG. 6 shows (a) a fluorescence spectrum ($\lambda_{ex}$=334 nm) of CCPE before mixing with GO and bacteria (initial, top line), after mixing with GO without bacteria ($F_{blank}$, bottom line), and after mixing with dsDNA-AuNPs with *E. coli* sample ($F_{sample}$, middle line); and (b) the percentage of fluorescence increase from the fluorimetric competition assay by using CCPE and GO as a function of *E. coli* (squares) and *S. aureus* concentration (circles).
Figure 7:
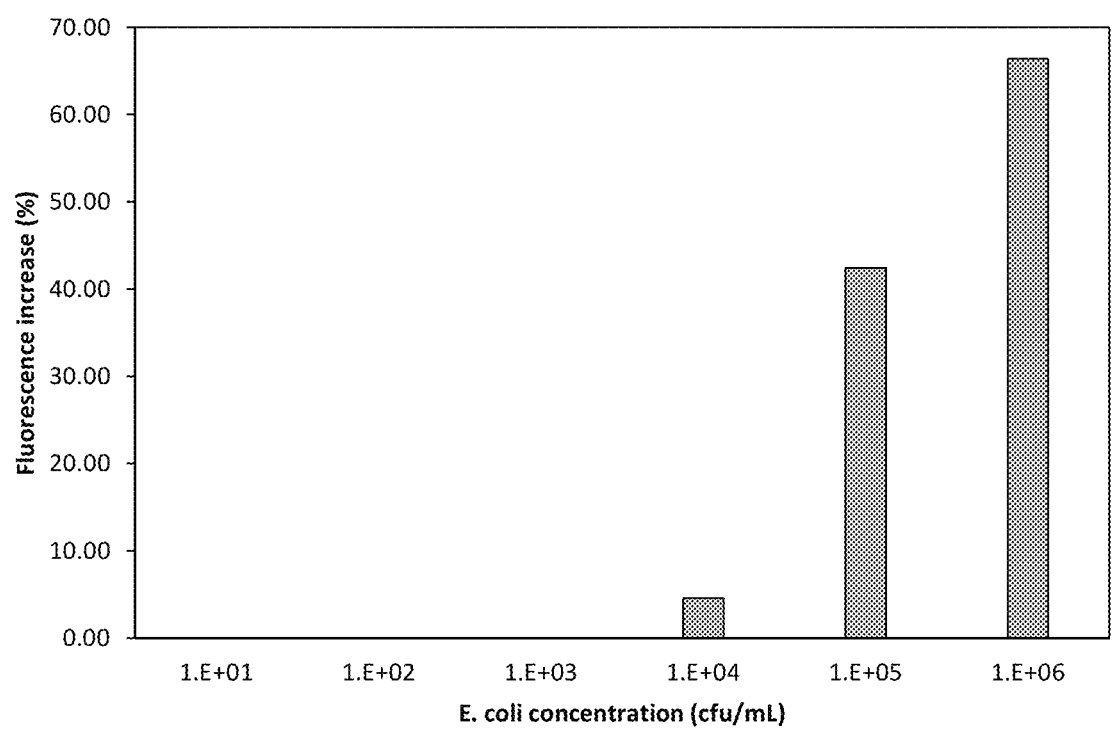
FIG. 7 shows the percentage of fluorescence increase from the fluorimetric competition assay by using peptide-FITC and GO as a function of live *E. coli* concentration.
Figure 8:
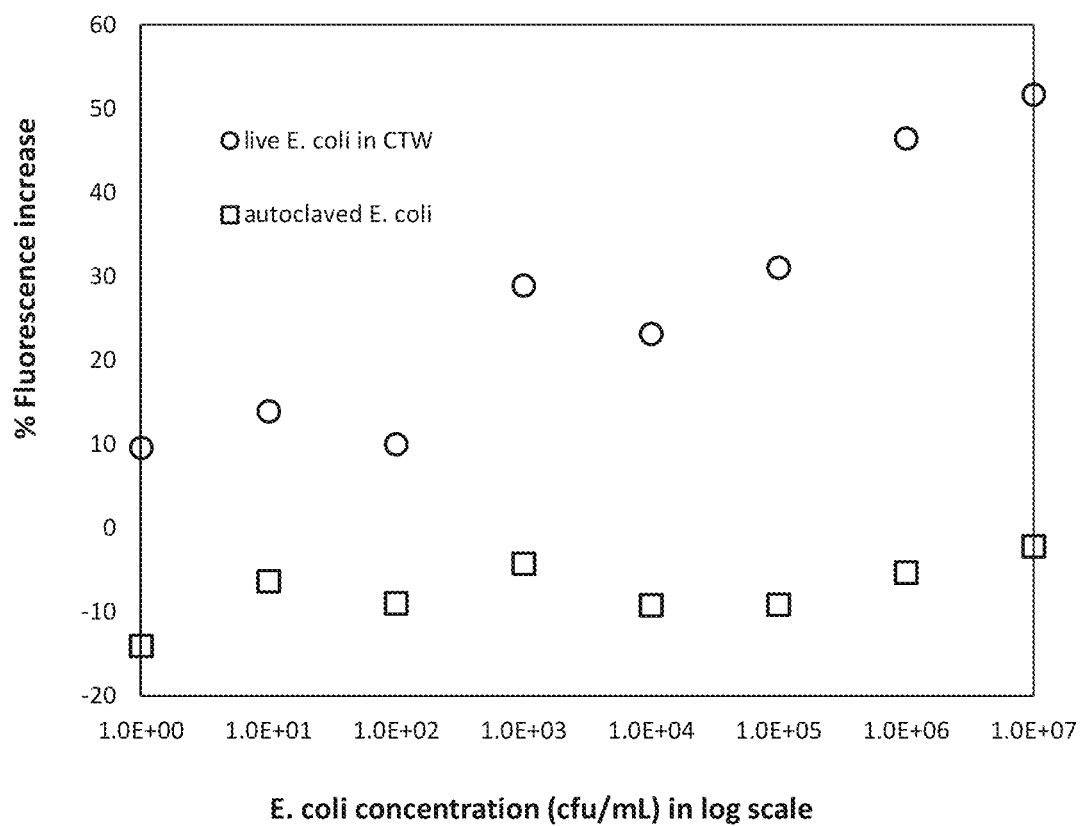
FIG. 8 shows the percentage of fluorescence increase from the fluorimetric competition assay by using CCPE and GO as a function of the concentration of live *E. coli* (dots) and dead-autoclaved *E. coli* (squares).
Figure 9:
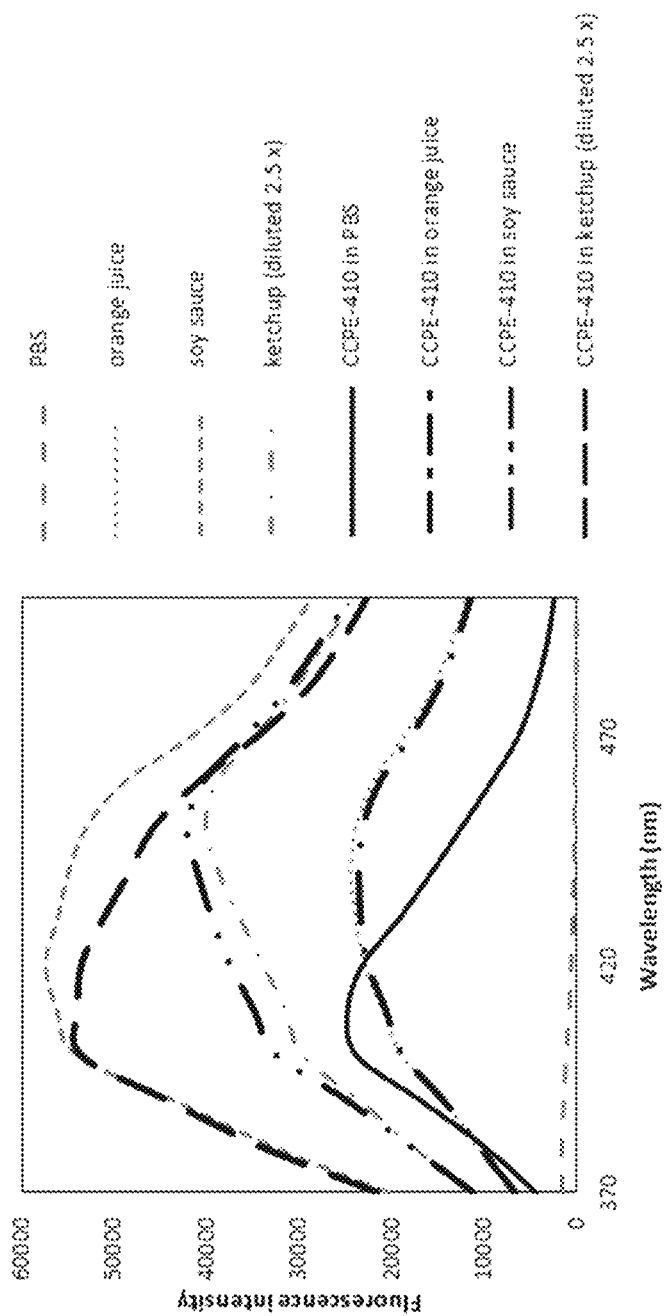
FIG. 9 shows the fluorescence spectra of PBS, pulpy orange juice, soy sauce, ketchup, and CCPE in these matrices. The auto-fluorescence background from juice, soy sauce, and ketchup mask the CCPE fluorescence intensity.
Figure 10:
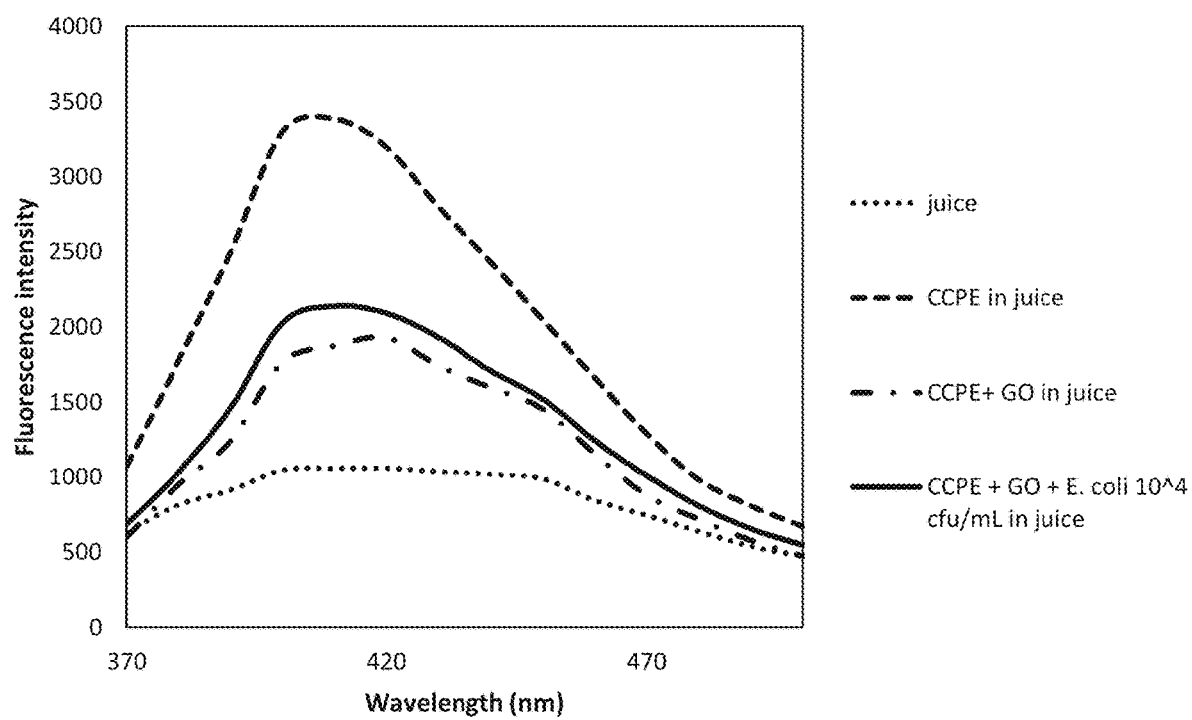
FIG. 10 shows the fluorescence spectra of 20 times diluted orange juice (bottom line), CCPE-410 in the diluted juice (top line), and CCPE-410 mixed with GO in diluted juice without ($3^{rd}$ from top line) and with *E. coli* sample in diluted juice ($2^{nd}$ from top line).
Figure 11:
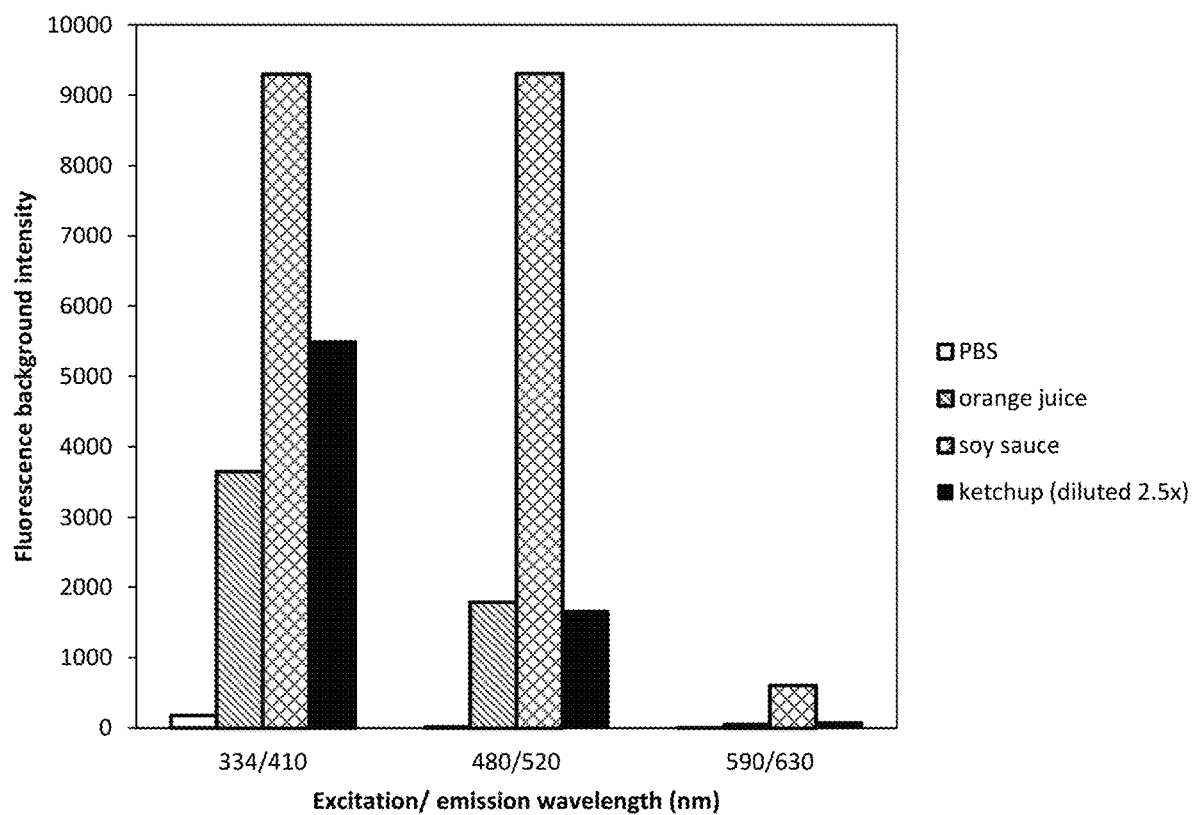
FIG. 11 shows the auto-fluorescence background intensity of PBS solution, pulpy orange juice, soy sauce, ketchup in various excitation/emission wavelength. Low fluorescence background intensity is observed in NIR region, where the excitation/emission conditions are at 590/630 nm.
Figure 12:
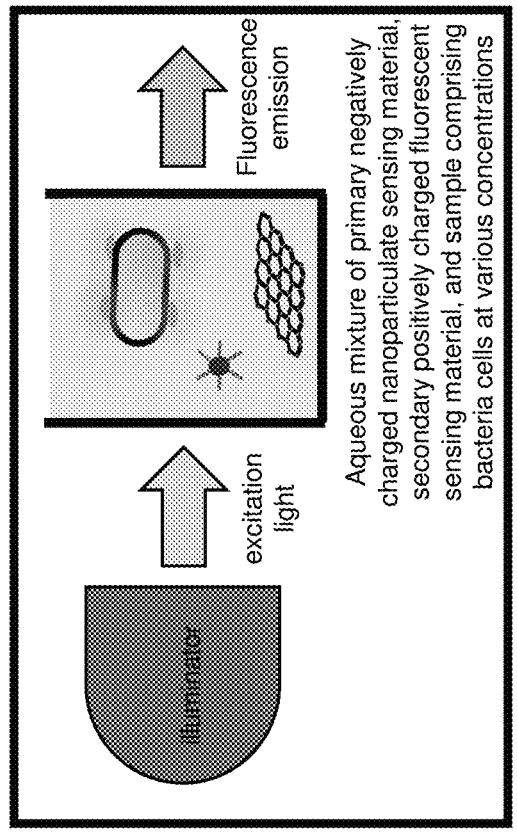
FIG. 12 shows a schematic diagram of a housing and at least one illuminator of the invention as described herein. The housing contains a primary negatively charged, nanoparticulate sensing material, a secondary positively charged, fluorescent sensing material and a sample potentially comprising bacteria in aqueous medium, while the illuminator provides light of at least one pre-specified wavelength $\lambda_i$ to excite at least the secondary positively charged, fluorescent material. The housing permits illumination of the contents of the housing by the illuminator and the housing further permits the detection of a fluorescent response at a second wavelength $\lambda_n$.

According to the invention a sensor has been provided that can detect and quantify the total amount of bacteria in water. This sensor may have numerous applications in the analysis of the hygienic status of industrial water, public recreational water, marine ballast water discharge or drinking water. The sensor may be used in environmental monitoring and may be used to indicate the exceeding of pre-set bacteria levels in samples. Depending on the sensing materials used the sensor may also be used to indicate whether bacteria in a sample are alive or dead.

The sensor and the related method further have a potential use in hygienic beverage or food analysis as interferences from colorations may be overcome.

The sensor and the related method can further serve as a platform technology. Through further development (e.g. modifying the surface of the sensing materials with bio-affinity materials etc.) technologies to target a specific bacteria type may be delivered to meet specific bacteria detection requirements.

It will be apparent that various other modifications and adaptations of the invention are available to the person skilled in the art after reading the foregoing disclosure without departing from the spirit and scope of the invention and it is intended that all such modifications and adaptations come within the scope of the appended claims.

The invention claimed is:

1. A sensor that detects bacteria cells comprising:
   a primary negatively charged, nanoparticulate sensing material;
   a secondary positively charged, fluorescent sensing material;
   a housing;
   and at least one illuminator;
   wherein said housing contains said primary negatively charged, nanoparticulate sensing material, said secondary positively charged, fluorescent sensing material and a sample comprising bacteria cells in aqueous medium,
   wherein said illuminator provides light of at least one pre-specified wavelength $\lambda_i$ to excite at least said secondary positively charged, fluorescent sensing material, wherein said secondary positively charged, fluorescent sensing material electrostatically attached to the bacteria cells provides at least one fluorescent response at a second different wavelength $\lambda_n$ wherein both i and n are integers, wherein said secondary positively charged, fluorescent sensing material is selected from the group consisting of cationic conjugated polyelectrolytes (CCPE), peptides labeled with fluorescence dye, and polymers labeled with fluorescence dye or being fluorescent, wherein said primary negatively charged, nanoparticulate sensing material electrostatically attached to said secondary positively charged, fluorescent sensing material suppresses fluorescing of said secondary positively charged, fluorescent material at said second wavelength $\lambda_n$;

wherein said housing permits illumination of the primary negatively charged, nanoparticulate sensing material, the secondary positively charged, fluorescent sensing material, and the sample comprising the bacteria cells in the aqueous medium by said illuminator and wherein said housing further permits detection of the at least one fluorescent response at said second wavelength $\lambda_n$, and wherein said second wavelength $\lambda_n$ is in the near infrared (NIR) region of the light.

2. The sensor according to claim 1, wherein said primary negatively charged, nanoparticulate sensing material is selected from the group consisting of metal nanoparticles and graphene oxide.

3. The sensor according to claim 2, wherein the metal of said metal nanoparticle is selected from the group consisting of gold and silver.

4. The sensor according to claim 2 wherein said metal nanoparticle is a metal nanoparticle to which dsDNA is conjugated.

5. The sensor of claim 1 wherein said cationic conjugated polyelectrolyte is selected from π-conjugated polymers comprising side chains with cationic groups.

6. The sensor of claim 5 wherein said cationic groups comprise moieties selected from the group consisting of quarternary ammonium and pyridinium.

7. The sensor of claim 5 wherein said π-conjugated polymer is selected from the group consisting of in each case cationic polythiophenes, poly(p-phenylene)s, poly(fluorene)s, poly(phenylene ethynylene)s, poly(fluorine ethynylene)s, poly(phenylene vinylene)s, poly(naphthalene vinylene)s, poly(fluorine vinylene)s, and copolymers thereof.

8. The sensor of claim 1 wherein said peptide comprises 5 amino acids to 100 amino acids and comprises amino acids selected from the group consisting of histidine, lysine, arginine, and mixtures thereof.

9. The sensor of claim 1 wherein said polymer comprises quaternary ammonium, biguanidine, phosphonium, guanidine, sulfonium, or pyridinium groups.

10. The sensor of claim 1 wherein said fluorescent dye is selected from the group consisting of Abz (Anthranilyl, 2-Aminobenzoyl), N-Me-Abz (N-Methyl-anthranilyl, N-Methyl-2-Aminobenzoyl), FITC (Fluorescein isothiocyanate), 5-FAM (5-carboxyfluorescein), 6-FAM (6-Carboxyfluorescein), TAMRA (Carboxytetramethyl rhodamine), Mca (7-Methoxycoumarinyl-4-acetyl), AMCA/Amc (Aminomethylcoumarin Acetate), Dansyl (5-(Dimethylamino) naphthalene-1-sulfonyl), EDANS (5-[(2-Aminoethyl)amino] naphthalene-1-sulfonic acid), Atto (Atto465, Atto488, Atto495, Atto550, Atto647), Cy3 (1-(5-carboxypentyl)-3,3-dimethyl-2-((1E,3E)-3-(1,3,3-trimethyl-indolin-2-ylidene)prop-1-en-1-yl)-3H-indol-1-ium chloride), Cy5 (1-(5-carboxypentyl)-3,3-dimethyl-2-((1E,3E,5E)-5-(1,3,3-trimethylindolin-2-ylidene)penta-1,3-dienyl)-3H-indolium chloride), Alexa Fluor (Alexa Fluor 647, Alexa488, Alexa532, Alexa546, Alexa594, Alexa633, Alexa647), Bodipy, Dylight (DyLight 488, DyLight 550), Trp (Tryptophan), Lucifer Yellow ((ethylene diamine) 6-Amino-2-(2-amino-ethyl)-1,3-dioxo-2,3-dihydro-1H-benzo[de]isoquinoline-5,8-disulfonic acid), and mixtures thereof.

11. The sensor of claim 1 wherein a detection principle is based on competitive electrostatic interaction or binding of the secondary positively charged, fluorescent sensing material with either the bacteria cells or the primary negatively charged nanoparticulate sensing material.

12. A method for detecting bacteria cells comprising the steps of:
(a) providing a system comprising:
  a. a primary negatively charged, nanoparticulate sensing material;
  b. a secondary positively charged, fluorescent sensing material that electrostatically attached to said primary negatively charged, nanoparticulate sensing material shows suppressed fluorescence; and
  c. at least one illuminator; wherein said secondary positively charged, fluorescent sensing material is selected from the group consisting of cationic conjugated polyelectrolytes (CCPE), peptides labeled with fluorescence dye, and polymers labeled with fluorescence dye or being fluorescent,
(b) adding a sample comprising bacteria cells in aqueous medium to the system;
(c) providing light of at least one pre-specified wavelength $\lambda_i$ to excite at least said secondary positively charged, fluorescent sensing material; and,
(d) detecting or measuring the fluorescence of said secondary positively charged, fluorescent sensing material at a second wavelength $\lambda_n$ after electrostatic attachment of the secondary positively charged, fluorescent sensing material to the bacteria cells in said sample, wherein said second wavelength $\lambda_n$ is in the near infrared (NIR) region of the light.

13. The method of claim 12 wherein the electrostatic attachment of the secondary positively charged, fluorescent sensing material to the bacteria cells competes with the electrostatic attachment of the secondary positively charged, fluorescent sensing material to the primary negatively charged nanoparticulate sensing material for at least 2 minutes and up to 30 minutes before detecting or measuring the fluorescence.

14. The method of claim 12 wherein the system additionally comprises a light detector and an analysis unit, wherein the analysis unit changes a status when the light detector signal exceeds a pre-set fluorescence value to indicate the presence of a certain concentration or total amount of total bacteria cells.

15. The method of claim 12 wherein said secondary positively charged, fluorescent sensing material has a charge density to achieve a pre-set fluorescence value that is identical to a desired detection limit of the bacteria cells.

16. The method of claim 12 wherein the method is used to detect whether said bacteria cells are alive or dead.

17. The method of claim 12 wherein a total bacteria count is detected.

18. The method of claim 12 wherein the bacteria cells comprise *E. coli* or *S. aureus* strains.

* * * * *

SEQUENCE LISTING

<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1

Glu Lys Ala His Asp Gly Gly Arg Tyr Tyr Arg Ala
1               5                   10